(12) United States Patent
Boese et al.

(10) Patent No.: US 7,590,442 B2
(45) Date of Patent: Sep. 15, 2009

(54) METHOD FOR DETERMINING THE POSITION OF AN INSTRUMENT WITH AN X-RAY SYSTEM

(75) Inventors: Jan Boese, Eckental (DE); Martin Kleen, Furth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 516 days.

(21) Appl. No.: 11/358,853

(22) Filed: Feb. 21, 2006

(65) Prior Publication Data

US 2006/0241413 A1 Oct. 26, 2006

(30) Foreign Application Priority Data

Feb. 21, 2005 (DE) .................. 10 2005 007 893

(51) Int. Cl.
*A61B 5/05* (2006.01)
*G06K 9/00* (2006.01)
(52) U.S. Cl. .................... 600/424; 378/62; 378/63; 382/128; 382/132; 382/154
(58) Field of Classification Search ............ 600/425, 600/407, 424; 378/21, 62, 64, 63; 382/128, 382/132, 154
See application file for complete search history.

(56) References Cited

U.S. PATENT DOCUMENTS

| 5,859,922 | A | 1/1999 | Hoffmann |
| 6,047,080 | A | 4/2000 | Chen et al. |
| 6,370,417 | B1* | 4/2002 | Horbaschek et al. ........ 600/424 |
| 7,050,844 | B2 | 5/2006 | Strobel |
| 2003/0014034 | A1* | 1/2003 | Strobel ........................ 604/407 |
| 2003/0181809 | A1* | 9/2003 | Hall et al. .................... 600/425 |
| 2003/0220555 | A1 | 11/2003 | Heigl et al. |
| 2006/0153468 | A1 | 7/2006 | Solf et al. |

FOREIGN PATENT DOCUMENTS

| DE | 44 17 414 A1 | 12/1994 |
| DE | 198 43 408 A1 | 3/2000 |
| DE | 101 14 099 A1 | 10/2002 |
| DE | 102 10 647 A1 | 10/2003 |
| DE | 102 40 727 A1 | 3/2004 |

* cited by examiner

*Primary Examiner*—Eric F Winakur
*Assistant Examiner*—Katherine L Fernandez

(57) ABSTRACT

The present invention relates to a method for determining the position of an instrument in a structure of an object with an x-ray system, in which a 3D image data record is provided for at least one area of the object relevant for determining the position, the x-ray system is registered with the 3D image data record, after the introduction of the instrument into the structure at least one 2D x-ray image of the relevant area is recorded from at least one direction of projection with a known projection geometry with the x-ray system and a 2D position of a first location of the instrument is recorded in the 2D x-ray image. In the method a projection line in accordance with the known projection geometry is placed through the 3D image data record at the 2D position and a 3D position of the first location of the instrument in the 3D image data record is determined from an intersection of the projection line with the structure. The method enables the 3D position to be determined with a simple monoplanar x-ray system.

11 Claims, 3 Drawing Sheets

METHOD FOR DETERMINING THE POSITION OF AN INSTRUMENT WITH AN X-RAY SYSTEM

CROSS REFERENCE TO RELATED APPLICATION

This application claims priority of the German application No. 10 2005 007 893.1 DE filed Feb. 21, 2005, which is incorporated by reference herein in its entirety.

FIELD OF THE INVENTION

The present invention relates to a method for determining the position of an instrument in a structure of an object, especially in a hollow canal or a hollow organ, with an x-ray system, in which a first 3D image data record is provided for at least one area of the object relevant for determining the position, the x-ray system is registered with the first 3D image data record, after the introduction of the instrument into the structure at least one 2D x-ray image of the relevant area is recorded from at least one direction of projection with a known projection geometry with the x-ray system, and a 2D position of a first location of the instrument is recorded in the 2D x-ray image.

BACKGROUND OF THE INVENTION

Interventional or surgical procedures performed with the aid of x-ray systems are required for numerous medical examinations or treatments. Radiological interventions are thus frequently undertaken for the diagnosis or treatment of vascular diseases, in which an instrument, especially a catheter, is fed through a peripheral blood vessel using x-ray illumination to the point of interest in the body. Controlling this type of instrument can sometimes be very demanding, especially if the blood vessels are very damaged and have many branches. To improve the navigation for the examining doctor this type of intervention is monitored as a rule with a monoplanar or biplanar imaging x-ray system. The x-ray images displayed during the intervention can in such cases map the position of the instruments, for example catheters, guide wires or stents, very exactly. With a suitable image processing method the position of the instrument can also be determined precisely.

When a monoplanar x-ray system is used however, the position of the instruments can only be determined in two dimensions. The three-dimensional position is unknown. The knowledge about the three-dimensional position of the instruments is however desirable in cases in which this position is to be displayed in an image representation of a 3D image data record which was previously recorded with a corresponding imaging modality. This type of overlaid display is of advantage for navigating the instrument.

Previously at least two x-ray images from different directions of projection have been required to determine the 3D position of an instrument or the tip of a catheter, as is described for example in US 2003/0220555 A1. This demands either the use of an expensive biplanar x-ray system or a time-consuming change in the angulation of a monoplanar x-ray system in conjunction with a sequential recording of two x-ray images from different directions.

A further previously known option for three-dimensional position determination of instruments demands the use of specific localization systems, employing electromagnetic sensors for example. A disadvantage of this method compared to x-ray imaging lies in the fact that only instruments equipped with specific sensors can be localized. Furthermore the number of instruments able to be localized as well as the number of sensors per instrument is restricted with these types of localization systems.

SUMMARY OF THE INVENTION

The object of the present invention is to specify a method based on x-ray imaging for three-dimensional position determination of an instrument in a structure of an object which is able to be carried out with a monoplanar x-ray system.

The object is achieved with the method in accordance with the claims. Advantageous embodiments of the method are the object of the subclaims or can be taken from the description below as well as from the exemplary embodiment.

In the present method a first 3D image data record of at least one area of the object relevant for position determination is provided, and the x-ray system is registered with the first 3D image data record. This registration makes a fixed assignment between the coordinate systems of the 3D image data record and the x-ray system. After the instrument has been introduced into the structure at least one 2D x-ray image of the relevant area is recorded from at least one direction of projection, with a known projection geometry with the x-ray system and a 2D position of a first location of the instrument being recorded in the 2D x-ray image. The instrument is visible in this x-ray image, so that the 2D position of a location of the instrument or of the tip of a catheter can be easily recorded. In the present method, at the recorded 2D position which for example can be marked in the display of the 2D x-ray image on a monitor by a user, a line of projection running in accordance the known projection geometry is preferably automatically placed through the first 3D image record or through a second 3D image record derived from it, which as a rule is also an image data record. The projection geometry (spatial position of x-ray focus and detector) is known as a result of the registration of the x-ray system with the 3D image record. A projection line is then a uniquely defined by the 2D position on the 2D x-ray image. The 3D x-ray image data record can be an original 3D image data record, a section of the 3D image data record restricted to the relevant area or also a further 3D image data record derived in another way, without changing the coordinate system, from the original 3D image data record. The derived 3D data record can for example be a data record with segmented image data—also in binary coded form—which is obtained by segmentation of the structures, for example blood vessels from the original 3D image data record. The 3D position of the first position of the instrument is finally determined from an intersection of the projection line with the structure in the 3D image data record or in the 3D data record derived from this.

The intersection can in this case be determined for example from the location of one or more maxima and/or minima of values, especially gray level values, for an image data record along the projection line in the first 3D image data record or second 3D image data record. For intersections which extend over a number of positions in the 3D data record, i.e. encompass a number of voxels, the 3D position is preferably determined from an averaging over these positions.

The present method makes use of the fact that as a rule the instruments can only stay within a restricted volume, above all in the corresponding structures, especially hollow canals or hollow organs, of the object. This restricted volume can be determined for the 3D image data record which was recorded before the position was determined using a suitable 3D imaging method. This 3D image data record can for example be recorded with a magnetic resonance (MR), computer tomography (CT), a 3D angiography, a Positron Emission Tomography (PET) or a 3D ultrasound system. When an appropriately embodied x-ray system is used, for example a C-arm device, the 3D image data record can also be recorded with the x-ray system itself.

The spatial position in three dimensions can be determined from the 2-dimensional position of the marked location of the instrument in the 2D x-ray image and the 3D image data. In this case it is naturally necessary for the corresponding structures to be able to be detected in the underlying 3D image data record. Depending on the recording and processing technology, for example subtraction angiography, these structures can then be present in the 3D image data record as areas with a local maximum of grey levels or a local minimum of grey levels. The current position of the point of interest is then determined in each case from the intersection point or the intersection points of the projection line with this type of structure.

With the current method it can occur that the projection line intersects the structures a number of times in the 3D image data record. The ambiguities which this produces in the 3D position determination can be remedied in a number of ways.

One option consists of showing the user a suitable representation of the 3D image data record with the projection line on a monitor so that the latter can choose the correct intersection point.

A further option consists of determining the most likely next position from the course of the previous 3D positions of the instrument over time. This is possible since in the main area of application of the current method, interventional or surgical procedures, a plurality of 2D X-ray images are recorded to trace the movement of an introduced instrument. The approximate new 3D position is in this case automatically restricted to a specific volume area starting at the previous 3D position.

In a further technique a number of locations of the instruments spaced from other are observed and their 3D position determined in accordance with the present method. If an ambiguity arises at one of these locations as a result of a number of intersection points of the projection line with the structure, this can be remedied as a rule by taking into account the 3D positions of the further locations.

The present method thus makes it possible to determine the 3D position of an instrument or a location of the instrument in a structure of an object with a simple monoplanar x-ray system. Monoplanar x-ray systems have the advantage of being less complicated and more flexible to use than for example biplanar x-ray systems. They are also able to be combined with magnetic navigation for example.

By contrast with localization systems which are not based on x-ray imaging, for example those using optical or electromagnetic sensors, determining the 3D position with an x-ray system has the advantage that no new instruments are required and all instruments able to be shown in x-ray images can be localized. In addition the positions of a large number of different locations of an instrument or a large number of different instruments can be localized in three dimensions with the present method.

Naturally more complex x-ray systems can also be used with the present method, such as biplanar x-ray systems or dual-focus x-ray systems, with the latter featuring a detector and also two x-ray focuses. The present method in such cases delivers an especially high level of accuracy in position determination if the two focuses of a dual-focus x-ray system lie close to each other and the two directions of projection of a biplanar x-ray system enclose an angle which is not 90°.

After the 3D position determination of the instrument the relevant position of the instrument can then be shown by marking it in a suitable or for example rendered display of the 3D image data record. The user can in this case, with a corresponding sequence of 2D x-ray images while the instrument is being guided through the structure, especially a body canal, trace the current position in this representation of the 3D image data record.

BRIEF DESCRIPTION OF THE DRAWING

The present method is explained again below on the basis of exemplary embodiments in conjunction with the drawings, without restricting the area of protection specified by the claims. The drawings show:

DETAILED DESCRIPTION OF THE INVENTION

The present example is designed to illustrate the monitoring of the guidance of a catheter in blood vessels of the patient in accordance with the present method. This type of catheter is restricted to vessel interventions in the area of blood vessels. In such a case for example 3D image data can be provided from a 3D angiography image of the patient.

This 3D image data record can in this case be recorded either before the introduction of the catheter or also after the introduction of the catheter directly before the first 3D position is determined. When an image is recorded after the introduction of the catheter, an x-ray system is required which makes it possible to record such a data record using 3D rotation angiography for example. In other cases the imaging modality for the recording of the 3D image data record can be completely independent of the x-ray system used for the intervention. The 3D image data record recorded is registered with the x-ray system used. In this case different known image registration methods can be used, as are known to the person skilled in the art from the prior art.

Figure 1:
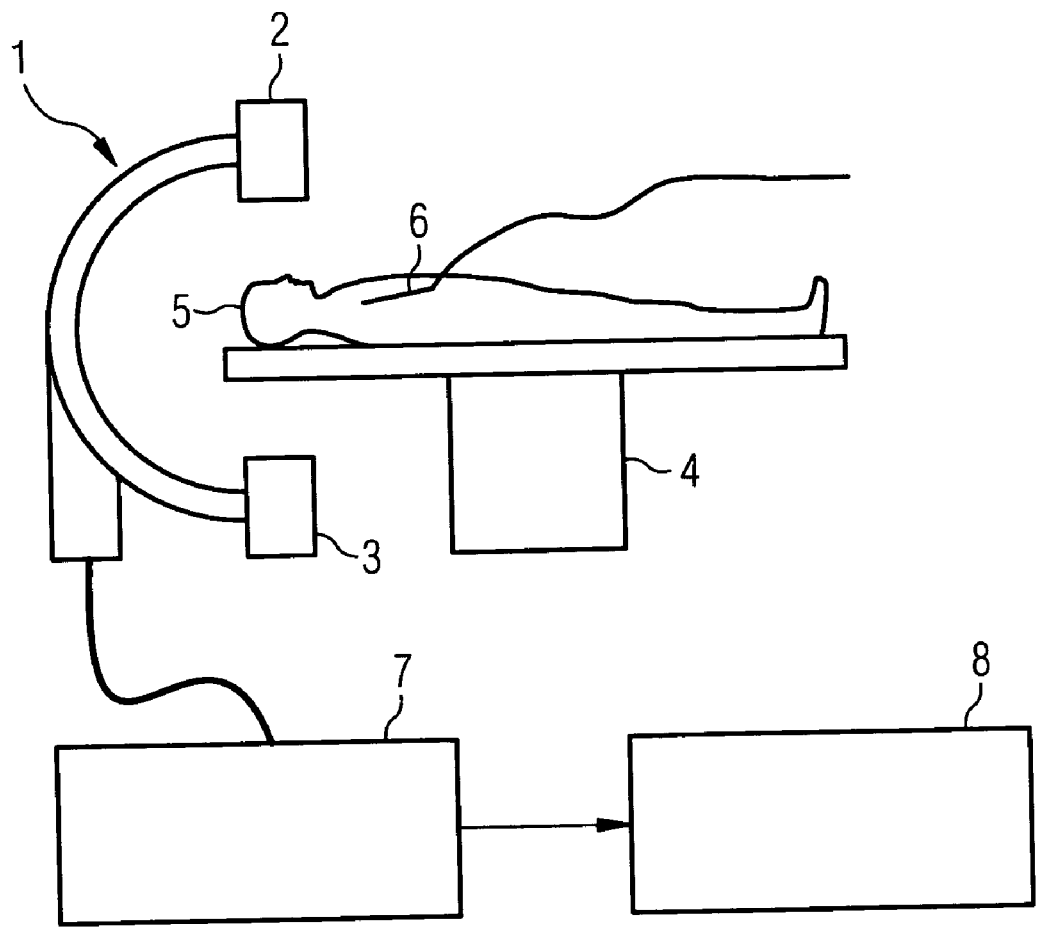
FIG. 1 a schematic diagram of a monoplanar x-ray system for monitoring an interventional procedure.

During the execution of the intervention which is shown in FIG. 1 for example, 2D x-ray images of the relevant area of the patient 5 are recorded at specific intervals with the x-ray system 1. FIG. 1 shows a typical monoplanar x-ray system 1 used for this purpose, with an x-ray tube 2 and an x-ray detector 3 opposite the tube. The patient 5 is supported on a patient support table 4 which allows movement. The catheter 6 to be localized is also shown schematically in this figure. The 2D x-ray images recorded are processed in the image processing unit 7 and displayed on an image display unit 8, which also permits user interaction via a graphical user interface. The 3D position is also determined in accordance with the present method in the image processing unit 7 which is fed to the 3D image data record.

Each time a new 3D position of the catheter 6 is determined, a 2D x-ray image is recorded with the x-ray system 1. The 2D x-ray image recorded is displayed to the user on the image display unit 8. The user can mark the tip of the catheter 6 in this displayed image in order to define the 2D position of this tip. Alternatively the position of the tip of the catheter 6 can be detected using a suitable image processing algorithm which recognizes this tip in the 2D image data record.

Figure 2:
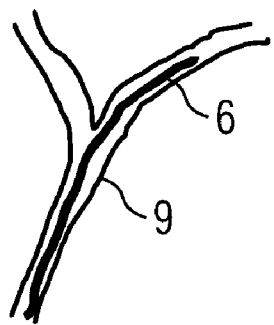
FIGS. 2 to 5 a first example for determining the 3D position using the present method.
Figure 3:
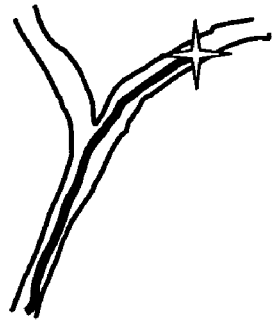

FIG. 2 shows a section from a 2D x-ray image in this connection in which a vessel 9 as well as the catheter 6 guided within it can be seen. In FIG. 3 the 2D position of the tip of the catheter 6 in the 2D x-ray image is marked with a cross.

Figure 4:
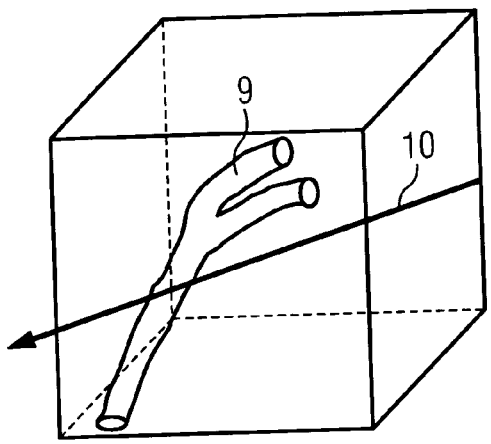

FIG. 4 shows schematically a section from the 3D image data record in which the progress of the vessel 9 can also be seen. This can involve a further processed 3D image data record which has been produced from the originally recorded 3D image data record by segmenting the vessel 9. This segmentation can be undertaken with a suitable segmentation method automatically or again through user interaction.

Figure 5:
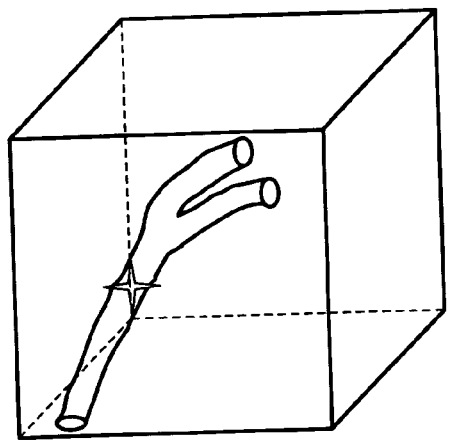

Subsequently a projection line 10 is placed through the 3D image data record. This requires knowledge of the projection geometry which can be taken to mean all position parameters of x-ray focus and x-ray detector, to enable the correct projection line between x-ray focus and x-ray detector to be obtained for the cone-shaped x-ray beam geometry for the selected image point. Registration of the x-ray system with the 3D image data record means that the course of the projection line is also known in the coordinate system of the 3D data record. This projection line 10 thus runs in accordance with the known projection geometry of the x-ray system (for the 2D imaging) and is further defined by the previously determined 2D position of the catheter tip. The intersection point of this projection line 10 with the vessel 9 in the 3D image data record is then determined as the current 3D position of the catheter tip, as shown by the cross in FIG. 5.

Since vessels can be detected in the 3D image data record on the basis of local maxima of the grey values, the intersection points with the projection line can be detected by determining the absolute or local maxima of the grey values along the projection line 10. This is illustrated in FIGS. 6 and 7.

Figure 6:
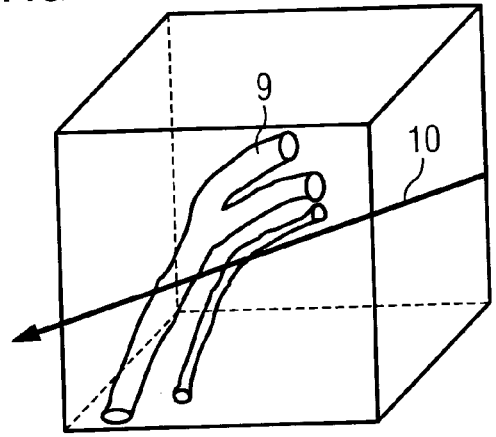
FIGS. 6 and 7 a second example for determining the 3D position using the present method.
Figure 7:
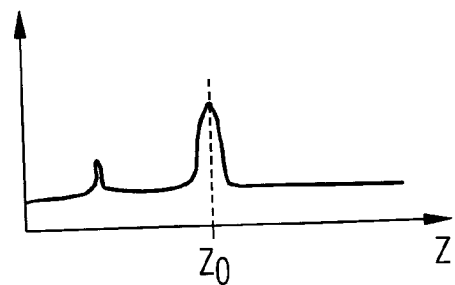

In FIGS. 6 and 7 a case is shown in which the projection line 10 intersects a number of vessels 9. In such a case the most probable 3D position at which the catheter tip is located is determined.

Thus the example of FIGS. 6 and 7 shows a case in which a vessel with a small diameter lies next to the main vessel used for the intervention. Such a case produces a sequence of grey values on the projection line 10, as is shown in FIG. 7. With such clear differences of the maxima, the value Z0 belonging to the highest maximum is included as the most probable value for determining the 3D position.

Figure 8:
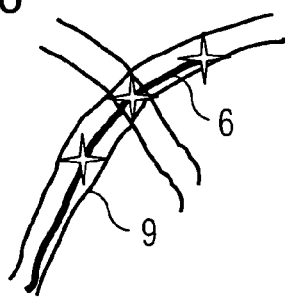
FIGS. 8 to 10 a third example for determining the 3D position using the present method.
Figure 9:
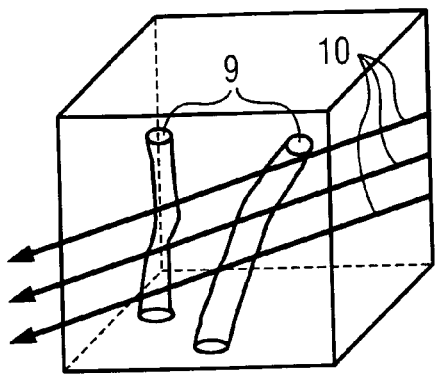
Figure 10:
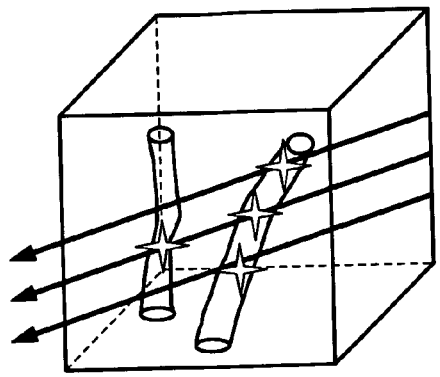

Another option with overlaid vessels lies in including a number of locations of the instrument for determining the 3D position. This is shown schematically in FIGS. 8 to 10. FIG. 8 again shows a section from a 2D x-ray image in which overlaid vessels 9 are shown. In this case three 3D positions of the catheter 6 are marked. The three projection lines 10 for these three 2D positions are entered in the 3D image data record shown in FIG. 9. Thus in this example it could not be established solely with reference to the average 2D position (cf. FIG. 8) and the associated projection line in which of the two vessels 9 shown the catheter 6 is moving. One of the two alternatives can however be discarded if the 2D positions of the two other locations and their projection lines are considered, as is indicated in FIG. 10. The average 3D position must in any event lie in the immediate vicinity of the 3D positions of the two adjacent locations of the catheter.

Figure 11:
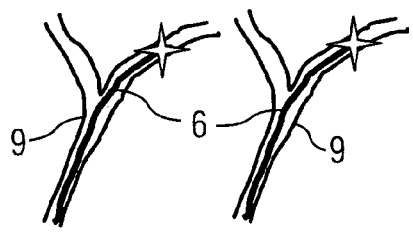
FIGS. 11 to 13 an example for determining the 3D position in accordance with the present method when using an x-ray system with two x-ray focuses.
Figure 12:
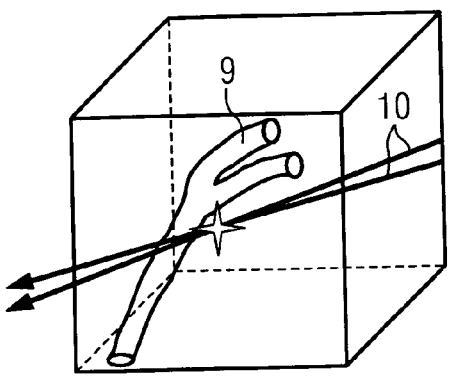
Figure 13:
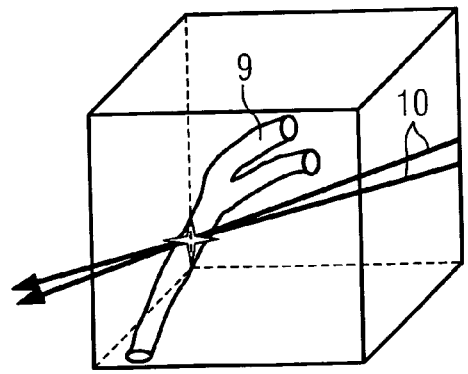

FIGS. 11 to 13 finally show an example of the use of the present method in connection with an x-ray system with two x-ray focuses, which lie almost adjacent to each other. With this type of x-ray system two 2D x-ray images are recorded in each case, of which the projection directions only differ by a small angle. FIG. 11 shows an example of two of these types of x-ray images in which the tip of the catheter is again marked in the vessel 9. If in this case corresponding projection lines 10 are placed through the 3D image data record, the position of the catheter tip can be derived directly from the intersection of the two projection lines 10. For x-ray focuses lying almost next to each other this determination is however very imprecise, such as the example of FIG. 12 shows. By using the present method in such a case, i.e. by determination of the intersection point of the relevant projection lines 10 with a vessel 9, this accuracy can however be improved. This is illustrated in FIG. 13. The same example can be transferred to the use of a biplanar x-ray system transmission, in which two x-ray images are likewise recorded from different projection directions.

The invention claimed is:

1. A method for determining a position of an instrument in a structure of an object with a x-ray system, comprising:
   providing a first 3D image data record of at least one area relevant for determining the position, the x-ray system is registered with the first 3D image data record;
   recording at least one 2D x-ray image of the relevant area after introduction of the instrument into the structure and from at least one projection direction with a known projection geometry with the x-ray system;
   recording a 2D position of a first location of the instrument in the 2D x-ray image with a projection line running in accordance with the known projection geometry being placed at the 2D position through the first 3D image data record or second 3D data record derived from it;
   using a processor to determine a 3D position of the first location of the instrument in the first 3D image data record or second 3D data record from an intersection of the projection line with the structure; and,
   wherein the intersection of the projection line with the structure is determined to locate the structure in which the instrument is positioned, and
   wherein the projection line intersects with a number of different structures providing a number of maxima and/or minima of grey level values along the projection line in the first 3D image data record or second 3D image data record, said determining the 3D position of the first location of the instrument including analyzing the grey level values.

2. The method in accordance with claim 1, wherein the object is a hollow canal or a hollow organ.

3. The method in accordance with claim 1, wherein the first 3D image data record is recorded with the x-ray system or another imaging modality.

4. The method in accordance with claim 1, wherein the second 3D data record is obtained from the first 3D data record by segmenting the structure.

5. The method in accordance with claim 1, wherein for a number of intersections of the projection line with the structure, the position of an intersection is selected as a 3D position which emerges as the most probable position taking into account at least one previous determination.

6. The method in accordance with claim 1, wherein at least one further 2D position of at least one further location of the instrument is recorded in the 2D x-ray image, at least one further projection line running in accordance with the known protection geometry is placed through the first 3D image data record or second 3D image data record at the at least one further 2D position, and a 3D position of the at least one further location of the instrument is determined from an intersection of the at least one further projection line with the structure.

7. The method in accordance with claim 6, wherein for a number of intersections of the first projection line with the structure, the position of one of the number of intersections is selected as the 3D position which, taking into consideration the intersection or intersections of the further projection line or projection lines counts as the most probable position.

8. The method in accordance with claim 1, wherein for a number of intersections of the projection line with the structure, the selection of the position of an intersection as a 3D position is possible by user interaction.

9. The method in accordance with claim 1, wherein for intersections which extend over a number of positions in the first 3D image data record or second 3D data record, an average position is selected as the 3D position.

10. The method in accordance with claim 1, wherein the 2D x-ray image is recorded with a monoplanar x-ray system.

11. The method in accordance with claim 1, wherein a biplanar x-ray system or an x-ray system with a detector and two x-ray focuses is used as an x-ray system, with which at least two 2D x-ray images being recorded from a different projection direction and evaluated for determining the 3D position.

* * * * *